US008506612B2

(12) United States Patent
Ashdown (10) Patent No.: US 8,506,612 B2
(45) Date of Patent: Aug. 13, 2013

(54) METHOD AND SYSTEM FOR PROVIDING ILLUMINATION AND PHYSIOLOGICAL STIMULI

(75) Inventor: Ian Edward Ashdown, West Vancouver (CA)

(73) Assignee: Koninklijke Philips N.V., Eindhoven (NL)

( * ) Notice: Subject to any disclaimer, the term of this patent is extended or adjusted under 35 U.S.C. 154(b) by 453 days.

(21) Appl. No.: 12/601,279

(22) PCT Filed: May 22, 2008

(86) PCT No.: PCT/IB2008/052031
§ 371 (c)(1),
(2), (4) Date: Nov. 23, 2009

(87) PCT Pub. No.: WO2008/146219
PCT Pub. Date: Dec. 4, 2008

(65) Prior Publication Data
US 2010/0174345 A1    Jul. 8, 2010

Related U.S. Application Data

(60) Provisional application No. 60/941,216, filed on May 31, 2007.

(51) Int. Cl.
*A61N 5/06* (2006.01)
(52) U.S. Cl.
USPC .......................................................... 607/88
(58) Field of Classification Search
USPC .......................................................... 607/100
See application file for complete search history.

(56) References Cited

U.S. PATENT DOCUMENTS

| | | | |
|---|---|---|---|
| 4,930,504 A * | 6/1990 | Diamantopoulos et al. | 607/88 |
| 6,350,275 B1 | 2/2002 | Vreman et al. | |
| 6,459,919 B1 * | 10/2002 | Lys et al. | 600/407 |
| 6,507,159 B2 * | 1/2003 | Muthu | 315/307 |
| 6,602,275 B1 * | 8/2003 | Sullivan | 607/88 |
| 2003/0223036 A1 | 12/2003 | Anderson et al. | |
| 2004/0052076 A1 * | 3/2004 | Mueller et al. | 362/293 |
| 2004/0232359 A1 | 11/2004 | Fiset | |
| 2010/0063566 A1 * | 3/2010 | Uchiumi et al. | 607/89 |

FOREIGN PATENT DOCUMENTS

DE    10359376 A1    7/2005

OTHER PUBLICATIONS

Figueiro et al., "Demonstration of additivity failure in human circadian phototransduction", Neuroendocrinology Letters, 2005, pp. 493-498, 26(5).
Figueiro et al., "Circadian effectiveness of two polychromatic lights in suppressing human nocturnal melatonin", Neuroscience Letters, 2006, pp. 293-297, 406(3).
Hurvich et al., "An opponent-process theory of colour vision", Psychological Review, 1957, pp. 384-404, 64.

* cited by examiner

*Primary Examiner* — Jessica Stultz
*Assistant Examiner* — Tuan Nguyen
(74) *Attorney, Agent, or Firm* — John F. Salazar; Mark L. Beloborodov (57) ABSTRACT

Disclosed herein are methods and systems for emitting light that can provide a desired light-induced physiological stimulus and a desired luminous stimulus. The light can be controlled to vary the physiological stimulus within a predetermined first range while maintaining the luminous stimulus within a predetermined second range that is useful for a number of self and/or space illumination applications. For example, an apparatus may include a controller for controlling the drive currents supplied to a plurality of light-emitting elements having different spectral characteristics, wherein the combination of currents is controlled such that the mixed light emitted is associated with the desired physiological and luminous stimuli.

11 Claims, 6 Drawing Sheets

METHOD AND SYSTEM FOR PROVIDING ILLUMINATION AND PHYSIOLOGICAL STIMULI

The invention pertains to lighting systems employing light-emitting elements and, more particularly, to lighting systems configured to provide illumination, as well as stimulate a desired light-induced physiological effect.

Traditionally, lighting systems have been employed solely to illuminate, i.e. to provide sufficient artificial light to be able to visually recognize features of the environment or, in case of direct-view systems, of the lighting system itself. Relatively recent research illustrates that light may also affect certain physiological functions of life forms and cause a number of physiological effects, as described, for example, in Figueiro "Research Matters", Lighting Design and Application 36(5), 15-17, 2006; Figueiro et al. "Demonstration of additivity failure in human circadian phototransduction", Neuroendocrinology Letters 26(5), 493-498, 2005; Figueiro et al. "Circadian effectiveness of two polychromatic lights in suppressing human nocturnal melatonin", Neuroscience Letters 406 (3), 293-297, 2006 (collectively, "Figueiro Publications"), all incorporated herein by reference. It has been shown that light may induce variations in, for example, general metabolism and sleep cycle of a number of life forms. Characteristics of light, such as its amount, particular spectral compositions as well as timing and duration of exposure to light, present important cues for the strength of light-induced physiological effects. Such characteristics are often referred to as light-induced physiological stimuli. It is noted, however, that physiological stimuli, in general, may include cues other than light. Specific physiological effects that are relevant or indicative of certain biochemical cycles of the metabolism and their effects in life forms throughout the day, for example, wake-sleep cycles, organ activity cycles and the like are often specifically referred to as circadian stimuli.

In general, circadian rhythms are physiological and behavioral oscillations that are normally synchronized with the natural light-dark cycle of the day. Circadian rhythm disorders are inappropriate or undesired circadian rhythms. Such disorders typically are related to sudden and/or extreme changes in the relationship between an organism's exposure to environmental light and its activity. Disruption to rhythms in the longer term is believed to have significant adverse health consequences on peripheral organs outside the brain, particularly in the development or exacerbation of cardiovascular disease. Timing of medical treatment in coordination with the body clock may significantly increase efficacy and reduce drug toxicity or adverse reactions. For example, appropriately timed treatment with angiotensin converting enzyme inhibitors (ACEi) may reduce nocturnal blood pressure and also benefit left ventricular (reverse) remodeling.

Circadian rhythm disorders are known to be associated with change in geographical location (jet lag) and night activity (graveyard shift workers). Another common type of circadian rhythm disorder is seasonal affective disorder (SAD), which is characterized by symptoms such as depression during the winter seasons when the duration of daylight is reduced. It has long been known that circadian rhythms in humans and other mammals are affected by exposure of the retina to light.

Accordingly, various techniques have been developed to treat circadian rhythm disorders by exposing the subject's eyes or tissues to light. Many of those techniques employ lighting sources configured to generate artificial light that closely simulates the intensity and spectrum of natural light and other dynamic light conditions. For example, one conventional device includes a collection of light sources of various colours controlled by a computer. The spectral qualities of the light produced by the light sources are measured and provided to the computer which then adjusts the light sources to generate the desired light conditions.

Another known device employs a plurality of light-emitting diodes (LEDs) at a particular distance from and oriented toward the subject; a portable power supply electrically connected to the LEDs; and a controller for altering the operation of the LEDs. The device is sufficiently light and compact to be comfortably worn by the subject. One or more such devices are used to deliver light to a subject's retinas, to the subject's vascular tissue, or simultaneously to both the retinas and the vascular tissue. For illumination of the retina, small LEDs are integrated into the frames of eyeglasses and positioned to direct light into the eyes of the subject. For illumination of the vascular tissue, an array of lens and LEDs is contained in a casing that is secured against the skin of the subject.

Also known are light sources configured to adjust or modulate human circadian rhythms and other photo-dependent body mechanisms. These light sources can generate light, for example, with spectral components having wavelengths distributed throughout the visible spectrum so as to be perceived by the human eye to be substantially white light. The energy of the light emitted by the source within an anomalous waveband around a wavelength of 460 nm may differ significantly from the energy emitted in any other waveband of equal width to enhance or suppress the modulation of human circadian rhythms.

It is generally known to control the alertness of human subjects by exposing them to suitable light radiation without substantially influencing the phase of a melatonin cycle. Melatonin is a sleep-hormone that can be used to control the alertness of a human subject. The suitable light radiation being specified by an output fraction of melatonin suppressive radiation (Melatonin Watt/Watt) and light output (lumen/Watt), the output fraction and light output being adjusted to obtain the desired effect on the phase of said cycle. For example, one conventional technique features a viewing screen coupled to a colour-limiting device. A programmable controller alters signals between an electronic device and a viewing screen to lower or eliminate a signal for a specific colour on the screen at specific times. Eliminating or lowering blue colour on the screen allows normal production of melatonin prior to normal sleep times to permit normal sleep cycles.

It is also known to adjust the circadian rhythm of a subject in a space by producing a variable light intensity level on a continuous basis from a light source. The light output from the source made available to the subject in the space is controlled in response to a control signal which varies in a manner corresponding to the solar and lunar altitude of a predetermined geographical location and the passage of time over a selected time interval of the day at predetermined geographical location.

Many of those approaches, however, focus solely on inducing desired physiological effect and, therefore, are poorly suitable for illumination. For example, Figueiro Publications recognized that short wavelength visible radiation (i.e., "blue" light) is primarily responsible for synchronizing the body's circadian rhythms and suggested the use of blue light to induce this beneficial effect. Unfortunately, the amount of short wavelength radiation emitted by common white light sources is rather low. Consequently, blue light by itself is much more efficacious in synchronizing the body's circadian rhythms than is white light, as shown in Table 1. Employing blue light, however, results in illumination that is unsuitable for most visual tasks.

TABLE 1

Common Light Source Photopic and Physiological Properties
(Figueiro Publications)

| Light Source | Photopic lumens/Watt | Circadian stimulus/Watt |
|---|---|---|
| Warm white fluorescent | 100 | 74 |
| Daylight fluorescent (7500K) | 100 | 157 |
| Incandescent | 12 | 12 |
| Daylight (6500K) | 70 | 133 |
| Blue LED | 15 | 418 |

Moreover, conventional systems and methods cannot provide a physiological stimulus within a desired range while also maintaining a certain luminous stimulus within a range that is useful for a number of self or space illumination applications. Therefore, there is a need for a new method and system for providing illumination and light-induced physiological stimulus that addresses shortcomings of conventional approaches.

Applicant herein has recognized and appreciated that it would be advantageous to provide a white light source whose spectral power distribution can be modified to increase or decrease its circadian stimulus per electrical watt as required. The light source could then be operated to provide energy-efficient space and/or self illumination in a normal mode, and, when desired, be capable of stimulating a desired light-induced physiological effect, for example, providing the maximum amount of blue light to synchronize circadian rhythms of a human subject.

Accordingly, one object of the invention is to provide a method and system for providing illumination and physiological stimulus. In accordance with an aspect of the invention there is provided a system for emitting light, the light providing a desired light-induced physiological stimulus and a desired luminous stimulus, the system comprising: one or more first light-emitting elements configured to emit light of a first wavelength range, the one or more first light-emitting element responsive to one or more first control signals; one or more second light-emitting elements configured to emit light of a second wavelength range, the one or more second light-emitting element responsive to one or more second control signals; and a control system operatively coupled to the one or more first light-emitting elements and the one or more second light-emitting elements, the control system configured to generate the one or more first control signals and the one or more second control signals based on the desired light-induced physiological stimulus, the desired luminous stimulus, the first wavelength range and the second wavelength range. The variation of the physiological stimulus may include varying emission of light having frequencies between about 420 nm and about 500 nm. In various embodiments, the desired luminous and physiological stimuli do not exceed predetermined limits or fall within predetermined value ranges.

In accordance with another aspect of the invention, there is provided a method for controlling light to provide a desired light-induced physiological stimulus and a desired luminous stimulus, the method comprising the steps of: generating light having a first wavelength range at a first intensity; generating light having a second wavelength range at a second intensity; adjusting the first intensity and the second intensity to generate mixed light having the desired light-induced physiological stimulus and the desired luminous stimulus.

In the drawings, like reference characters generally refer to the same parts throughout the different views. Also, the drawings are not necessarily to scale, emphasis instead generally being placed upon illustrating the principles of the invention.

Unless defined otherwise, all technical and scientific terms used herein have the same meaning as commonly understood by one of ordinary skill in the art to which this invention belongs. Specifically, the term "light-emitting element" (LEE) is used to define a device that emits radiation in a region or combination of regions of the electromagnetic spectrum for example, the visible region, infrared and/or ultraviolet region, when activated by applying a potential difference across it or passing a current through it, for example. Therefore a light-emitting element can have monochromatic, quasi-monochromatic, polychromatic or broadband spectral emission characteristics. Examples of light-emitting elements include semiconductor, organic, or polymer/polymeric LEDs, optically pumped phosphor coated light-emitting diodes, optically pumped nano-crystal light-emitting diodes or other similar devices as would be readily understood by a worker skilled in the art. Furthermore, the term light-emitting element is used to define the specific device that emits the radiation, for example a LED die, chip or other such device as will be readily understood by the person of skill in the art, and can equally be used to define a combination of the specific device that emits the radiation together with a dedicated or shared substrate, driving and/or optical output means of the specific device(s), or a housing or package within which the specific device or devices are placed.

The term "luminous stimulus" is used herein to refer to one or more aspects of light as visually perceived by a human observer. For example, colour, brightness, luminance, intensity, luminous flux, chromaticity, correlated colour temperature (CCT) and the like can be considered luminous stimuli, as would be understood by a worker skilled in the art. Although light may visually stimulate different observers in different ways, it is common practice to use standardized metrics to evaluate various luminous stimuli. A number of luminous stimuli or indicators thereof, for example, luminous efficacy, luminance, luminous flux, intensity, correlated colour temperature ("CCT"), color rendering indices ("CRI"), and chromaticity under either photopic, scotopic or mesopic conditions are known in the art and standardized for various well-defined observation conditions. For example, CCT is typically defined as the temperature of a Planckian radiator whose perceived colour most closely resembles that of a given stimulus at the same brightness and under specified viewing conditions.

The term "light induced physiological stimulus" or "physiological stimulus" is used herein to refer to a characteristic of light, such as amount, certain spectral compositions as well as time and duration of exposure, which can be important cues for the strength of light-induced physiological effects. It is noted, however, that physiological stimuli, in general, may include cues other than light. Specific physiological effects that are relevant or indicative of certain biochemical cycles of the metabolism and their effects in life forms throughout the day, for example, melatonin metabolization, wake-sleep cycles, organ activity cycles and the like are often specifically referred to as circadian stimuli.

In its various embodiments and implementations, the invention relates to methods and systems for emitting light providing a desired light-induced physiological stimulus and a desired luminous stimulus. The light can be controlled to vary the physiological stimulus within a predetermined first range while maintaining the luminous stimulus within a predetermined second range that is useful for a number of self or space illumination applications. For example, in some embodiments, a controller is provided for controlling the drive currents supplied to a plurality of light-emitting elements having different spectral characteristics, wherein the combination of currents is controlled such that the mixed light emitted is associated with the desired physiological and luminous stimuli.

In accordance with embodiments of the present invention, the system for emitting light which provides light-induced physiological stimulus and luminous stimulus includes one or more first light-emitting elements, one or more second light-emitting elements and a control system. The one or more first light-emitting elements are configured to emit light of a first wavelength range and are responsive to one or more first control signals. In addition, the one or more second light-emitting elements are configured to emit light of a second wavelength range and are responsive to one or more second control signals. The control system is operatively coupled to the one or more first light-emitting elements and the one or more second light-emitting elements and is configured to generate both the first and second control signals. For the generation of these control signals, the control system is configured to use information representative of the desired light-induced physiological stimulus and the desired luminous stimulus, together with information indicative of the first wavelength range and the second wavelength range. The control signals evaluated by the control system can be used to control the first light-emitting elements and the second light-emitting elements in order that light having a desired light-induced physiological stimulus within a first range and a desired luminous stimulus within a second range can be generated.

Figure 1:
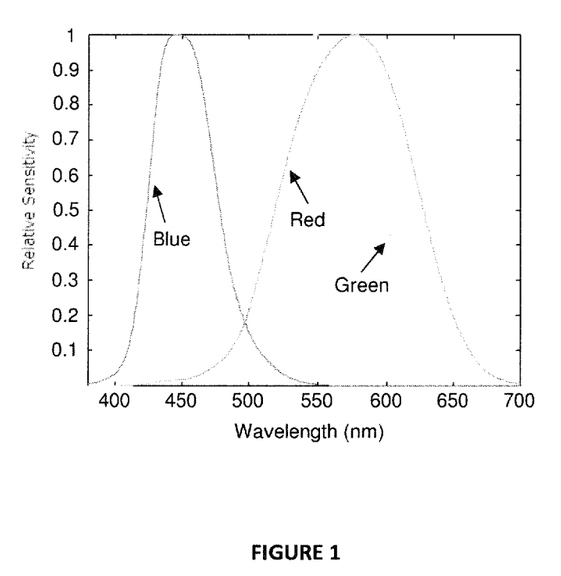
FIG. 1 illustrates Stockman cone fundamentals for colour vision.

Typically, humans can perceive mixed light from multi-colour light sources exhibiting different spectral power distributions (SPDs) as "white" light because the colour sensors, or cones, in our retina are responsive within fairly wide and overlapping regions of the visible spectrum. For example, the "Stockman cone fundamentals" chart illustrated in FIG. 1 shows the spectral sensitivity of different types of cone receptors of the eye. What is perceived as substantially white light can be a highly variable spectral composition. For example, certain continuous broadband spectra such as that of daylight or even those with distinct spectral peaks such as the light emitted by a number of narrowband chromatic light sources such as red, green, and blue LEEs may be perceived as white light.

Figure 2:
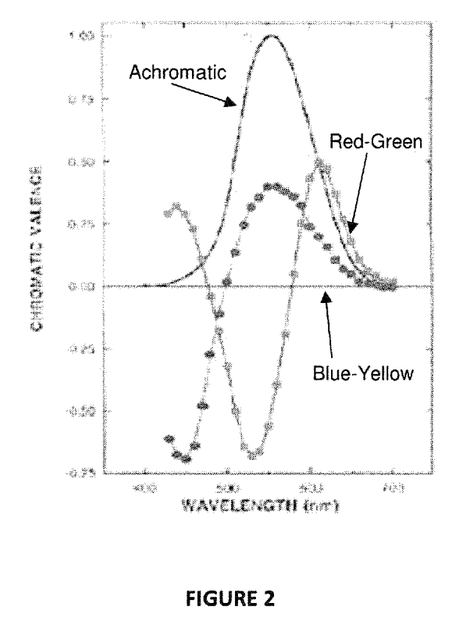
FIG. 2 illustrates typical opponent process graphs for red-green and blue-yellow chromatic valence as well as the achromatic response for a standard human observer.

Light-induced physiological stimuli may correlate with the amounts of radiation emitted in specific blue and green regions of the visible portion of the electromagnetic spectrum, and are often independent of the amount of radiation in other spectral regions. As skilled artisans would readily appreciate, human and some other species can perceive colour largely because of certain sensitivities of the visual system to differences in strengths of radiation at certain different wavelengths. This sensitivity of the visual system is typically known as colour opponency and is discussed by Hurvich et al. in "An opponent-process theory of colour vision," Psychological Review 64: 384-404, 1957, incorporated herein by reference. FIG. 2 illustrates typical opponent process graphs for red-green and blue-yellow chromatic valence as well as the achromatic response for a standard human observer.

Figure 3:
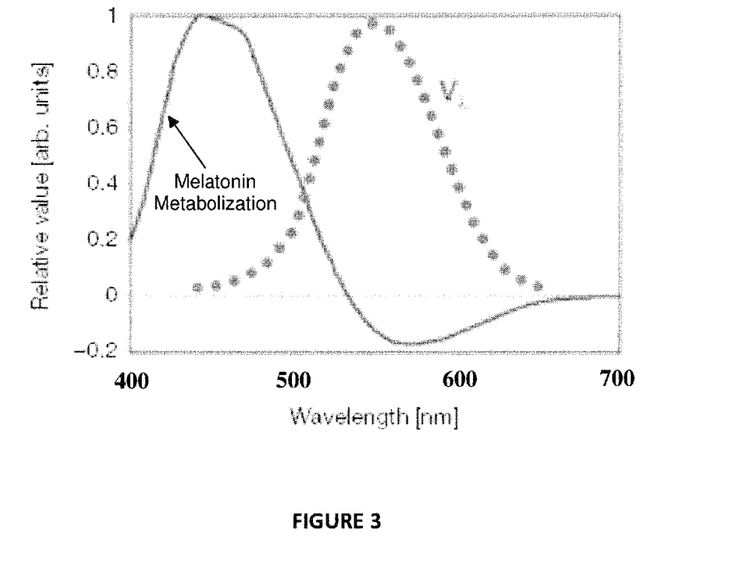
FIG. 3 illustrates a spectrally resolved physiological stimulus in comparison to the achromatic photopic efficacy curve $V_\lambda$ of the human eye.

It is noted that there are a number of physiological effects known to be responsive to certain circadian stimuli and that different stimuli may cause different physiological effects. Physiological effects may include different levels of metabolizing certain kinds of hormones including hormones which may affect or control sleep, cell metabolism, immune reactions and the like. An exemplary physiological stimulus efficacy curve is shown in FIG. 3 which generally illustrates the sensitivity of melatonin metabolization as a function of wavelength as discussed by Rea in "A Second Kind of Light", Opto Photonic News, October 2006, pp. 35-39, incorporated herein by reference. This curve peaks at about 440 nm (blue) and has a local minimum at about 570 nm.

It has been observed that two SPDs can exhibit substantially similar luminous effects but can elicit very different physiological effects. For example, different white lights can exhibit similar intensity and correlated colour temperature (CCT) while acting substantially differently as physiological stimuli. For example, in an embodiment of the invention a RGB LEE-based luminaire has two blue LEEs with peak wavelengths at about 440 nm and about 480 nm, respectively. Either one as well as both blue LEEs can be used to generate white light of a wide range of CCTs when used in combination with red and green LEEs. While the perceived photometric intensity of the 480 nm peak wavelength blue LEE, however, is six times that of the 440 nm peak wavelength blue LEE, the circadian stimulus shown in FIG. 3 at 480 nm blue light is about 60% that of 440 nm blue light. Depending on the ratio of 440 nm and 480 nm blue light, the corresponding circadian stimulus due to a multi-colour LEE-based light source system can be controlled over about one order of magnitude without typically any perceptible change in luminous stimuli such as perceived intensity, luminous flux or CCT, by varying the relative intensities of the 440 nm and 480 nm peak wavelength blue LEEs. It is noted that the same principle applies when combining such blue LEEs with LEEs of other colours such as warm white, blue, and green.

Generally, changing from light of certain first spectra to light of certain second spectra may affect physiological stimuli to a greater extent than it affects, if at all, a desired luminous stimulus. For example, in one embodiment, the present invention can be used to maintain an adequately high quality white light associated with a predetermined luminous stimulus, for example, a predetermined intensity, CCT, CRI, or chromaticity, while it can also affect a significant physiological effect via variation of a respective physiological stimulus.

Figure 4:
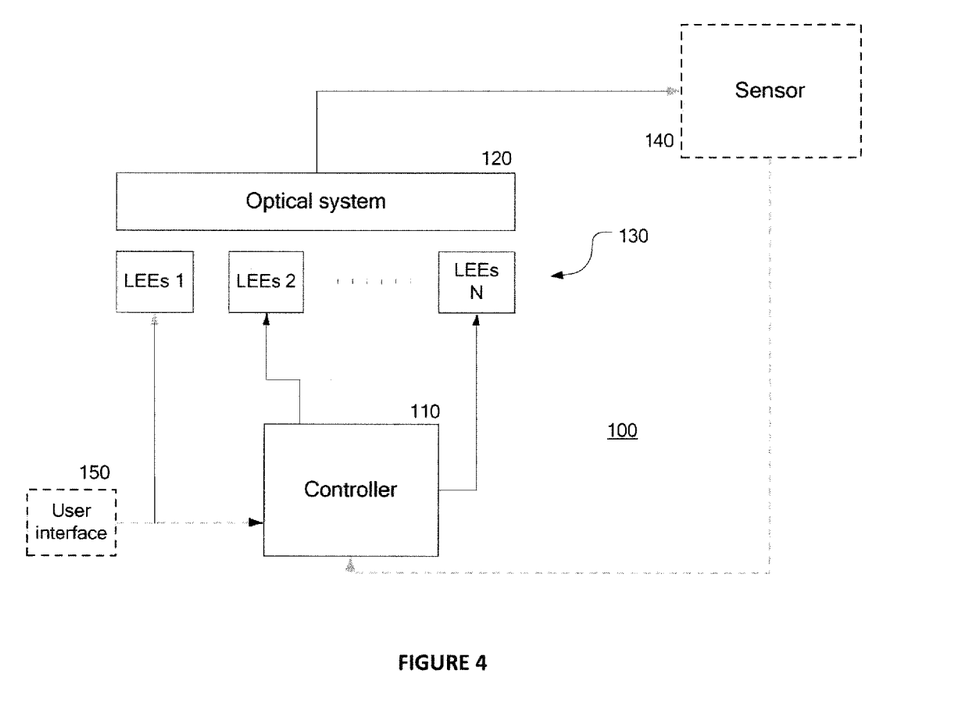
FIG. 4 illustrates a block diagram of architectures of a system according to an embodiment of the invention.

FIG. 4 illustrates the architecture of an LEE-based lighting system 100 according to various embodiment of the present invention. The lighting system includes LEEs 130 of N different colours, a controller 110 and an optical system 120. In many embodiments, the light source includes LEEs 130 of at least two different colours. Any one of LEEs 130 can emit, for example, red, green, blue, amber, magenta, yellow, cyan, white light, or other coloured light or combination of colours. The optical system 120 is designed to efficiently capture and mix light emitted by the multi-colour LEEs. The system 100 may include an optical sensor system 140 for evaluating the spectral composition of the mixed light. The optional optical sensor system 140 can be operatively coupled to an adequately configured controller and the combination used to control the light-emitting elements in an optical feedback fashion. The lighting system may also include a user interface 150 for providing certain parameters supplied by a user during operation. The lighting system 100 can be used for various general purpose space and/or self illumination applications such as in fixtures/luminaires or in display devices such as screens, panels, monitors or projectors.

The present invention also focuses on a method for controlling an LEE-based lighting system such that it can generate light having both desired luminous and physiological stimuli and/or such that the desired luminous and physiological stimuli do not exceed predetermined limits or fall within predetermined value ranges. The light generated by the LEE-based light source can provide both luminous and physiological stimuli either simultaneously or alternatingly. In the latter case, for example, the light source may provide desired first luminous and physiological stimuli at one time while providing either the luminous or physiological stimulus at another time. In other words, the light source can be configured to provide only the desired physiological stimulus that is generally unsuitable for illumination and not provide the desired luminous stimulus, as defined above. The light source can also be configured to provide variable levels or variable types of luminous and/or physiological stimuli. In some embodiments of the invention, this variability is imperceptible to the observer.

While some metrics for reproducibly quantifying physiological/circadian stimuli exist, refined metrics for quantifying circadian stimuli are being developed in the art. Different metrics can be employed in the present invention through, for example, reconfiguration of the controller or selection of adequate LEEs as would be readily understood by a worker skilled in the art. A number of luminous stimuli, for example, luminance, luminous flux, intensity, CCT, CRI and chromaticity under either photopic, scotopic or mesopic conditions are known in the art and standardized for various well defined observation conditions. Luminous efficacy, the ratio of luminous flux to radiant flux, is also a similarly known, standardized and potentially useful indicator of luminous stimuli.

In one embodiment, the light emitted by the LEEs can interact with the components of the lighting system. It may be refracted and absorbed at different rates as determined by corresponding refractive and absorptive indices at different wavelengths. The optical system can be designed to exploit such effects to properly mix the light from the different LEEs into an adequate, homogenous beam of radiation that is suitable for the desired illumination application. The light provided by the optical system, while approximately being a sum or superposition of the light provided by each LEE, may exhibit practically relevant, possibly undesired features of the spectral composition of the emitted light due to absorption, refraction, diffraction, chromatic aberration and the like inside the light source system. In one embodiment, the controller can be configured to compensate for undesired spectral features in order to maintain the desired luminous and physiological stimuli in the emitted light irrespective of whether an open or closed optical loop is employed to control the light. For example, the controller may compensate for relatively higher amounts of absorption of short wavelength light by the light source system by increasing the intensity of light emitted by those LEEs which directly emit or cause the generation of that short wavelength light.

Besides LEEs of different colours, different types of LEEs may be employed in the light source system. For example, the light source system may employ broad spectrum warm white light, i.e. low CCT, LEEs in combination with narrow spectrum blue and green LEEs. As a further example, the light source may employ only red, green and blue LEEs. Adequately controlled LEEs of different colour can be used to desirably vary physiological and luminous stimuli, for example, intensity, CCT or chromaticity of the mixed light.

The light-emitting elements can be rapidly turned ON and OFF. For a wide variety of illumination applications the transients between ON and OFF cycles can be practically considered instant. As is known, LEEs can therefore be effectively controlled in a number of different ways. For example, the perceived brightness of light emitted by LEE can be controlled by rapidly pulsing the drive current between ON and OFF states of the LEE. Typical examples of pulsed drive current control include pulse width modulation (PWM) and pulse code modulation (PCM). Adequate PWM can be used for precise brightness control over a large dynamic range. Typically, PWM and PCM methods utilize drive current trains with either a fixed frequency or pulse duration and switch drive currents between zero (OFF) and a fixed finite (ON) value while varying either the duty cycle or the pulse train density. There are a large number of variations of PWM and PCM methods in which drive current amplitudes or frequencies may be varied, or in which a finite non-zero OFF current may be utilized. As is known, flicker of light from sufficiently rapidly pulsed LEEs is typically imperceptible. The respective lower frequency limit, also called the critical fusion frequency, is subject to certain conditions of the observer and may vary between individuals and different species. Humans typically cannot perceive brightness fluctuations above about 100 Hertz. As is also known, the human visual system is less susceptible to certain variations in colour/chromaticity than to brightness fluctuations. LEEs can also be controlled by varying the amplitude of a continuous drive current. Different embodiments of the invention may employ these or other forms of drive current control.

In some embodiments, the controller controls the LEE drive currents for the N different colours of LEEs in accordance with a drive current method. It is noted that more than one LEE may be employed per colour. In one embodiment, with respect to the light emitted by each LEE, the controller may be either a feed forward (open optical loop) or a feedback (closed optical loop) controller. An optical feedback controller typically requires an adequate optical sensor system to be able to evaluate, at least to a certain extent, the spectral composition of the emitted light. Moreover, in one embodiment, the light source system may comprise one or more temperature or forward voltage sensors to provide information indicative of the operating temperature of the LEEs or other operating characteristics for example, and the controller may be configured as a temperature feedback controller accordingly, irrespective of the use of an open or closed optical loop. The forward voltage of many types of LEEs can be used to adequately accurately evaluate LEE junction temperature. A number of other forms of temperature sensors would be known to a worker skilled in the art.

In one embodiment, the controller may be configured according to an adequately accurate model of the components of the LEE-based light source system in order to be able to desirably and accurately control the emitted mixed light in, at least in part, an open optical loop manner. The model may include parameters such as nominal colour and spectral bandwidth of each LEE, temperature drift and spectral broadening of each LEE, junction temperatures for each LEE, and drive current luminous flux response functions of each LEE, and the like. In embodiments with an optional optical sensor, the controller may be optionally configured in accordance with dynamic characteristics inherent in the drive current vs. luminous flux response functions to evaluate dynamic drive current control with reduced undesired side effects and thereby accomplish more rapid and stable feedback control.

The controller may include a number of components including microprocessors, microcontrollers, CPUs, programmable logic devices, drivers, constant current sources, voltage stabilizers, and the like in order to provide adequate pulsed or continuous drive currents for the LEEs. The controller is also configured to determine drive currents based on the desired luminous and circadian or physiological stimuli and it may be able to provide and switch between different methods of operation to provide the desired stimuli.

In one embodiment, the controller can be operatively coupled to a memory device. For example, the memory device can be integrated into the controller or it can be a memory device connected to the controller via a suitable communication link. In a further embodiment, the controller can store the required voltage and/or current magnitudes of previously determined drive voltages and/or currents in the memory device for subsequent use during operation of the apparatus. The memory device can be configured as an electronically erasable programmable read only memory (EEPROM), electronically programmable read only memory (EPROM), non-volatile random access memory (NVRAM), read-only memory (ROM), programmable read-only memory (PROM), flash memory or any other non-volatile memory for storing data. The memory can be used to store data and control instructions, for example, program code, software, microcode or firmware, for monitoring or controlling the one or more devices which are coupled to the controller and which can be provided for execution or processing by the CPU associated with the controller.

In embodiments of the present invention, the controller can be adequately configured to determine drive currents for each LEE colour such that the mixed light provides desired luminous and physiological stimuli, for example circadian stimuli, in ways as described above. For example, the controller can include a stimulus control module configured to determine, based for example on user input or other instructions, whether a physiological stimulus is desired and, if so, a desired amount and type of stimulus to be induced by the illumination system. The stimulus control module can further be configured to determine amounts of light from each type to provide the physiological stimulus, while maintaining one or more luminous stimuli in a desired range, and to influence the drive currents of the light-emitting elements appropriately.

For example, if the stimulus control module determines that substantially no physiological stimulus is desired, the controller can cause the light-emitting elements to be driven to provide illumination having desired luminous stimuli, without particular regard to providing physiological stimuli. The desired luminous stimuli can, in one embodiment, be determined based on input to the controller, for example due to user input. If the stimulus control module determines that a particular physiological stimulus is desired, the controller can cause a selected combination of light-emitting elements to be driven using selected currents to provide the desired stimulus. The light-emitting elements and drive currents can be selected by the stimulus control module in conjunction with the controller, such that the physiological stimulus and one or more desired luminous stimuli fall within a predetermined desired range, if possible. If the desired physiological stimulus and the desired luminous stimuli cannot be provided due to limitations of the illumination system such as the gamut of light emitted by the light-emitting elements, then the stimulus control module can adjust one or more of the desired physiological stimuli and the desired luminous stimuli in a predetermined manner until a feasible illumination within acceptable ranges for both luminous stimuli and the physiological stimuli can be found. For example, a lower than desired level of physiological stimuli may be induced to preserve illumination at a desired level.

In one embodiment, the controller can be configured to deliver the desired current waveforms directly to the light-emitting elements operatively coupled thereto by using current drivers integrated into the controller.

In another embodiment, the controller can be configured to deliver control signals to current drivers, the control signals configured to induce the current drivers to deliver the desired current waveforms to the light-emitting elements operatively coupled thereto.

Figure 5:
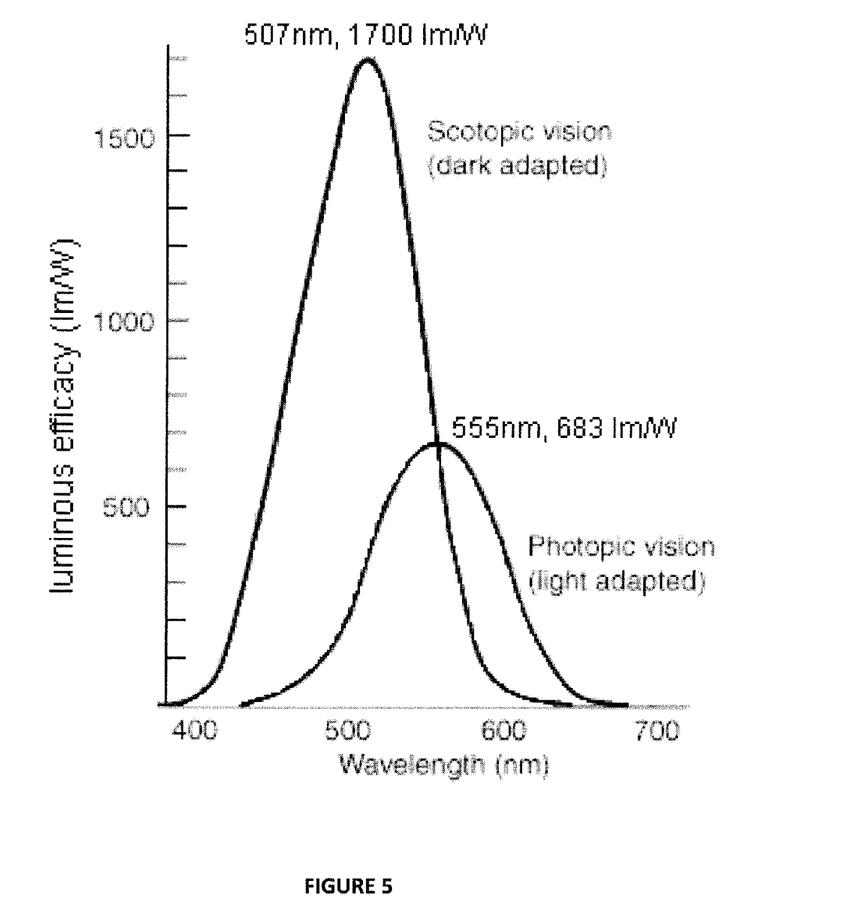
FIG. 5 illustrates commonly accepted representative photopic and scotopic statistical average achromatic responses of the human eye as a function of wavelength.

A physiological stimulus provided by light of a given spectrum can be evaluated similarly to intensity or chromaticity by adequately transforming the spectrum of the light emitted by the light source based on a physiological stimulus model. The spectrally resolved sensitivity of an example physiological stimulus is illustrated in FIG. 3. FIG. 5 illustrates commonly accepted representative photopic and scotopic statistical average responses of the human eye as a function of wavelength. These response characteristics can be used to determine the luminous efficacy of light by weighting the spectral distribution of the light of interest with the respective physiological, photopic, mesopic, or scotopic response and evaluating the average weighted values, either by, for example, integration or, approximately, by summation of the weighted values at discrete intervals or other method, as skilled artisans would readily appreciate.

The invention generally takes advantage of one or more empirical physiological stimulus models of certain physiological effects, each using a certain spectral physiological stimulus function. In one embodiment, these functions can be used to evaluate an expected physiological effect by evaluating the weighted average or other function of the spectral distribution of the light in question. It is noted that determining a physiological stimulus may require information about the strength of the radiation in the visible as well as certain near visible portions of the spectrum of the mixed light. It is also noted that the strength of radiation at some near visible wavelength regions may have little or no effect on luminous stimuli such as intensity or chromaticity. It is also noted that an instant physiological stimulus may need to be combined with other information such as timing, duration and strength to be able to accurately assess potential physiological effects.

A spectral distribution of light, such as a spectral radiant power distribution, can be transformed to provide a measurement of physiological or luminous stimulus in several ways. For example, a scalar value representing a stimulus such as melatonin metabolization or luminous flux can be mathematically derived from a spectral radiant power distribution through weighted integration, weighted summation, or other operation as would be understood by a worker skilled in the art. As another example, vector-valued functions representing tristimulus or chromaticity values can similarly be derived by an appropriate operation.

In one embodiment, the controller can be configured with a model of the lighting system as well as respective models for luminous and physiological stimuli for each of one or more predetermined operational modes of the system. The controller can monitor operational conditions of the system, for example, temperature, device aging, amount of ambient light, and use them in the form of parameters in these models to evaluate adequate LEE drive currents to generate light with the desired luminous and physiological stimuli. The desired stimuli may be predetermined or, optionally, provided in real time during operation via a user interface.

The relationship between stimuli, operational parameters and drive currents may exhibit highly non-linear characteristics but can be resolved in approximate and practically sufficient ways by using a number of different methods. For example, the controller may employ standard analytical and non-analytical as well as constrained and unconstrained equation solvers, fuzzy logic, neural network models, and the like to solve the system of equations describing the non-linear characteristics of relations between stimuli, parameters and drive currents.

As mentioned above, the light source may generally provide desired first luminous and physiological stimuli at one time while providing either the luminous or physiological stimulus at another time. In other words, the light source can be configured to provide only the desired physiological stimulus that is generally unsuitable for illumination and not provide the desired luminous stimulus, as defined above. The light source can also be configured to provide variable levels or variable types of luminous and/or physiological stimuli.

In one embodiment, a desired light-induced physiological stimulus can be provided continuously at the same time along with a desired luminous stimulus, such as luminous flux, intensity, colour, chromaticity, CRI, and/or CCT. In another embodiment the controller is configured to control the LEEs such that the spectral composition is modulated with additional bursts of light of adequate spectral composition to improve physiological stimulus while minimally affecting the desired time averaged luminous stimulus. The switching may be performed in different ways by adequately selecting duration and frequency of the bursts. It is noted that, depending on the brightness of the light, the human visual system is generally less perceptive to variations in colour or chromaticity than it is to brightness variations. In one embodiment, therefore, luminous stimuli indicative of brightness are varied within a smaller range than luminous stimuli indicative of colour or chromaticity, thereby enabling lower perceptible variation in illumination.

In one embodiment, the controller is configured to achieve a desired physiological stimulus while maintaining the desired luminous stimulus at a predetermined level or within a predetermined range about a predetermined level. If this is not possible, different embodiments of the controller may be configured to respond differently. For example, the controller may be configured to override certain limits for desired luminous stimulus in order to achieve a desired physiological stimulus, or, alternatively, it may inhibit physiological stimuli that cannot be achieved without overriding limits of luminous stimulus. Other responses are possible, as would be readily understood by skilled artisans, for example overriding limits of different stimulus by different amount based on a predetermined priority or weighting of priorities in order to determine a feasible illumination with acceptable levels of each stimulus.

It is also noted that only light of certain intensity within a specific spectral range may effectively contribute to a certain physiological stimulus. In one embodiment, the bandwidth of the spectral sensitivity or weighting characteristics of a physiological stimulus may be important when determining the dominant wavelengths and bandwidths of the LEEs to be employed in the lighting system.

In one embodiment, drift of the dominant wavelength of the LEEs and the broadening of the bandwidth of the LEEs under varying operating conditions may require employing groups of certain chromatic LEEs with similar but different nominal dominant wavelengths in order to broaden the spectrum of the light emitted by a group. This configuration can ensure that intensity variations in the spectrum of the light emitted by the whole group can still cause significant variations in the physiological stimulus even if the spectrum of one or more LEEs of the group no longer overlap with the respective spectral physiological response function. For example, sufficiently large numbers of adequately binned chromatic LEEs can provide an adequate nominal dominant wavelength spread to desirably widen the spectrum.

Examples 1, 2 and 3 specify example configurations of LEEs that can be integrated into a lighting system in accordance with embodiments of the present invention. A lighting system would include the required components, software, hardware, firmware and the like in order to appropriately control these example configurations of LEEs.

One exemplary LEE-based light source system employs red, green and blue LEEs that can emit light which provides a higher physiological stimulus than a broadband white light source emitting light of substantially the same photopic luminous flux. For example, the photopic luminous flux of a light source can be expressed by weighting the radiant flux of the light source at each visible wavelength by the luminous efficacy (as illustrated in FIGS. 3 and 5) at that wavelength, and summing or integrating the results over a predetermined range of visible wavelengths.

Because the luminous flux is determined by summing or integrating contributions over a range of wavelengths, two light sources, for example a LEE-based light source comprising red, green and blue LEEs and a broadband white light source, can have substantially the same total luminous flux but substantially different spectral distributions. Similarly, physiological stimulus can be expressed by weighting the radiant flux of a light source at each visible wavelength by a physiological response function (for example melatonin metabolization as illustrated in FIG. 3) and summing or integrating the results over a predetermined range of wavelengths. Therefore, since the weighting functions for luminous flux or efficacy and physiological response (for example melatonin metabolization) can substantially differ, it is possible to configure the different spectral power distributions of the two light sources such that the physiological stimuli substantially differ while the luminous flux remains substantially the same.

Another exemplary LEE-based light source system employs blue LEEs with two or more different nominal dominant wavelengths and one or more green and one or more white LEEs and is configured such that the physiological stimulus of the emitted light can be varied without varying the luminous efficacy or chromaticity. As described above, a selected first blue LEE can deliver a higher proportion of its output at wavelengths eliciting a visual stimulus than a selected second blue LEE, whereas the green and white LEEs can deliver comparatively little of their output at wavelengths eliciting the visual stimulus. By varying the relative amounts of light emitted by the first and the second blue LEEs, the amount of visual stimulus can thus be varied.

At substantially the same time, the amounts of light emitted by the green and white LEEs can be adjusted accordingly to retain substantially the same luminous efficacy or chromaticity. For example, to maintain luminous efficacy, if the relative amounts of blue light are adjusted such that the luminous efficacy of the combined blue light decreases, then the amounts of green and white light can be adjusted to deliver a corresponding increase of luminous efficacy of the combined green and white light. The increases and decreases in luminous efficacy can be configured to substantially cancel, thereby retaining a substantially constant luminous efficacy overall.

Figure 6:
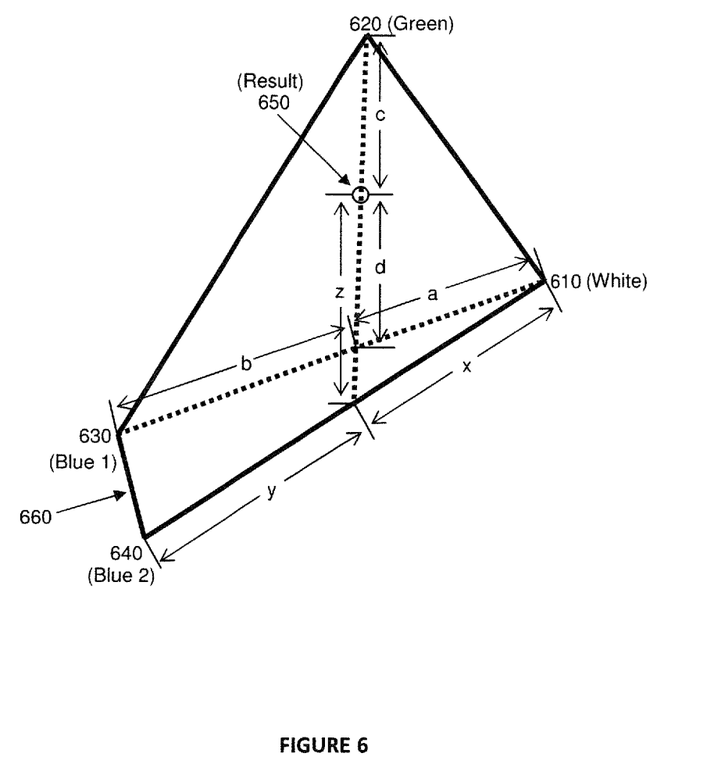
FIG. 6 illustrates a portion of a CIE chromaticity diagram showing mixtures of different sets of light-emitting elements to obtain a desired chromaticity.

As another example, FIG. 6 illustrates a portion of a CIE chromaticity diagram, wherein light from a white LEE, a green LEE, and two blue LEEs is combined to yield a resultant light. The chromaticities of the white, green, first blue and second blue LEEs are at vertices 610, 620, 630 and 640, respectively. If the resultant chromaticity can accurately be expressed as a convex combination of chromaticities of the individual LEEs, then the chromaticity at point 650 can be achieved using only one of the blue LEEs as follows. If only the first LEE having chromaticity 630 is used, then the (intensity) proportion of blue to white light can be a/b, and the proportion of the combined blue and white light to green light can be c/d. If only the second blue LEE having chromaticity 640 is used, then the (intensity) proportion of blue to white light can be x/y, and the proportion of the combined blue and white light to green light can be c/z. If both blue LEEs are used, the chromaticity at point 650 can similarly be achieved by considering an equivalent blue LEE having a chromaticity along line segment 660, the chromaticity determined by a convex combination of chromaticities 630 and 640, weighted in accordance with the relative intensities of the two blue LEEs.

Depending on the desired luminous and physiological stimuli, the lighting system may employ many different combinations of LEE colours, as discussed in detail below.

Still another exemplary LEE-based lighting system includes green LEEs with two or more different nominal dominant wavelengths and one or more blue and one or more white LEEs and is configured such that the physiological stimulus of the emitted light can be varied without varying one or more luminous stimuli. For example, the relative intensities of one or more LEEs can be varied as in Example 2 to vary a physiological stimulus, while the remaining LEEs can be varied in compensation to hold the luminous efficacy or chromaticity substantially invariant.

Yet another exemplary LEE-based lighting system includes red, green, blue and amber LEEs or red, green blue and white LEEs and is configured such that the physiological stimulus of the emitted light can be varied without varying one or more luminous stimuli. For example, the relative intensities of one or more LEEs can be varied as in Example 2 to vary a physiological stimulus, while the remaining LEEs can be varied in compensation to hold the luminous efficacy or chromaticity substantially invariant.

The LEE-based lighting system may also employ green, blue and warm white LEEs and is configured such that the physiological stimulus of the emitted light can be varied without varying one or more luminous stimuli. For example, the relative intensities of one or more LEEs can be varied as in Example 2 to vary a physiological stimulus, while the remaining LEEs can be varied in compensation to hold the luminous efficacy or chromaticity substantially invariant.

In various embodiments of the invention, the luminous flux can be held substantially fixed while varying the physiological stimulus as discussed in connection with Examples 2-3. For example, FIG. 3 illustrates that melatonin metabolization stimulation can be increased by increasing the radiant intensity of light between about 400 nm and about 525 nm. However, to maintain a substantially constant luminous flux, the radiant intensity of light between about 525 nm and 650 nm must be increased such that the luminous flux, for example as represented by the total integrated power spectral density weighted by the luminosity function $V_\lambda$, remains substantially constant. In other words, an increase in intensity of light at lower wavelengths can be balanced by a corresponding decrease in intensity of light at higher wavelengths, in order to maintain substantially constant luminous flux. Moreover, it is noted that, with respect to melatonin metabolization in FIG. 3, both actions (increasing intensity at lower wavelengths and decreasing intensity at higher wavelengths) can increase this physiological stimulus, due to the negative (inhibiting) response of melatonin metabolization at higher wavelengths.

Figure 7:
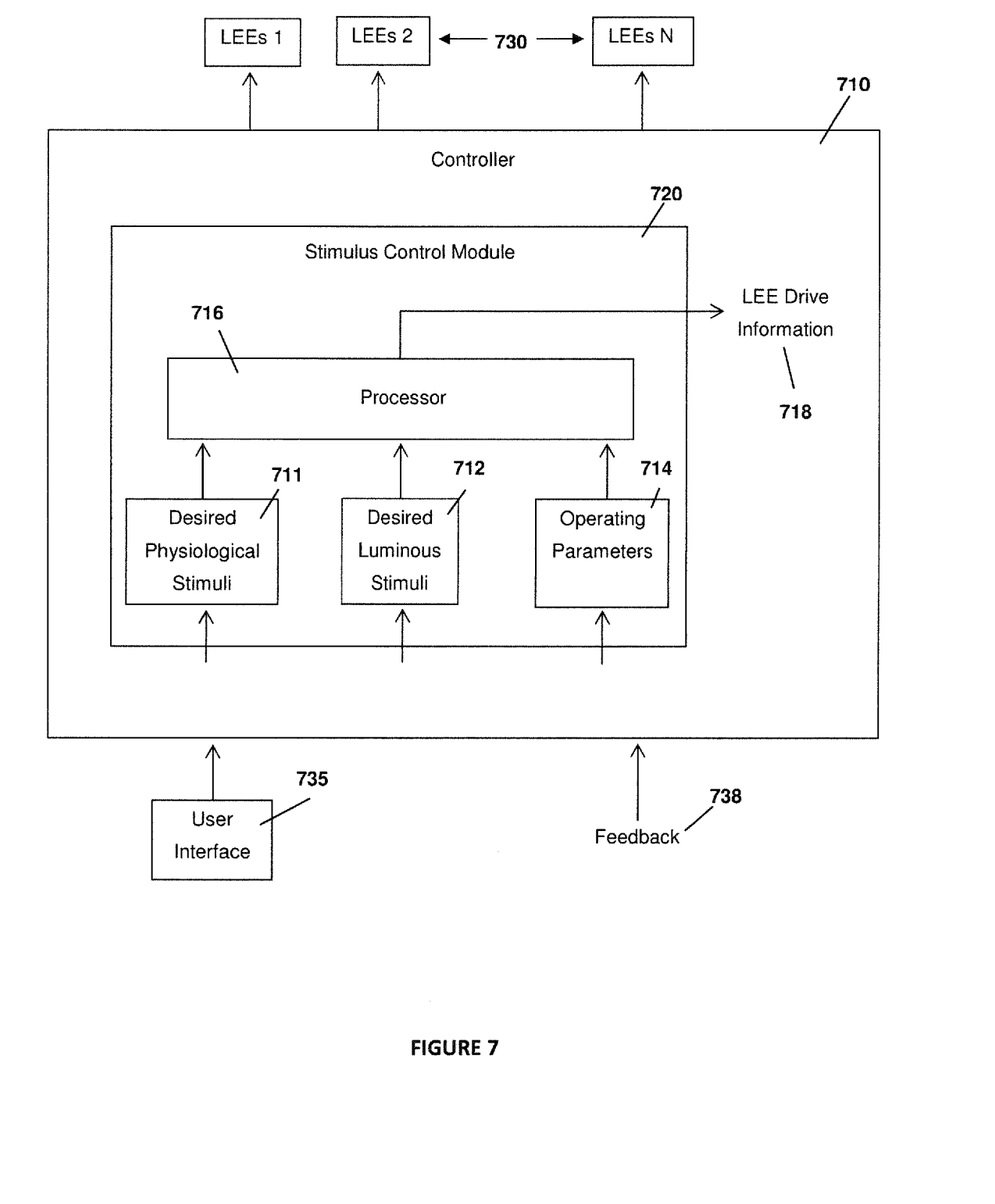
FIG. 7 illustrates a system for providing illumination and physiological stimulus according to an embodiment of the present invention.

FIG. 7 illustrates a system according to a particular embodiment of the present invention, having a stimulus control module 710 directed toward controlling the drive current to produce a desired physiological stimulus while maintaining desired luminous stimuli. The stimulus control module 710 is operatively coupled to a controller 720, the control module providing drive currents to N light-emitting elements 730. The controller 720 accepts input from a user interface 735 or other source of information, as well as optional feedback 738 from one or more sensors coupled to the light-emitting elements directly or through an optical system (not shown). Input from the user interface 735 and feedback 738 is provided to the stimulus control module 710 in the form of desired physiological stimuli 711, desired luminous stimuli 712, and operating parameters 714. The inputs to the stimulus control module 710 can characterize variables in the illumination system, such as desired characteristics of the illumination and current capabilities of the light-emitting elements, due to device heating, ageing, ambient lighting, and the like.

The desired stimuli 711 and 712 and operating parameters 714 are provided as inputs to a processor 716, which determines appropriate LEE drive information 718, for example drive current waveform control, that can induce one or more aspects of illumination based on the desired stimuli 711 and 712 and in light of operating parameters 714. For example, if it is feasible to provide light in accordance with all desired stimuli 711 and 712, the LEE drive information 718 may result in drive current waveform control resulting in said light, provided the operating parameters remain amenable to such activity. If at least one stimulus is not feasible, the processor 716 may determine alternative LEE drive information 718 deemed acceptable by a predetermined metric. For example, the processor 716 can determine a solution for LEE drive information 718 which results in selected stimuli being substantially close to or within their desired operating regions, while other selected stimuli may be substantially neglected or farther from their desired operating regions. As another example, a feasible solution for LEE drive information 718, given current operating parameters 714, can be computed by assigning one or more values to one or more selected stimuli and calculating LEE drive information 718 which substantially minimizes the distance, or otherwise falls within a predetermined feasible distance, from the values to a desired operating region for the stimuli in a vector space, such that the solution falls within a feasible region defined by the current operating parameters.

For example, if the stimulus control module 710 determines, due for example to input from the user interface 735, that a physiological stimulus A (such as inducing melatonin metabolization) is desired at a specified level, wherein physiological stimulus A requires providing light in a frequency band around about 450 nm, then the stimulus control module can compute LEE drive information 718 which results in an increase in light emitted by blue LEEs producing light in this frequency band, the increase in accordance with the specified level of the stimulus A. If it is further specified that the luminous flux and chromaticity are to remain within a prespecified range, then the stimulus control module can compute LEE drive information 718 which boosts LEEs producing light in other frequency ranges to compensate for the change in blue light, provided a feasible compensation solution can be found. If a feasible solution cannot be found, for example if boosting LEEs in other frequency ranges would result in exceeding operational limits of the LEEs, then the prespecified operating conditions, for example the level of stimulus A or the luminous flux or chromaticity ranges, can be adjusted and a new feasible solution sought.

The processor 716 can include a microprocessor or microcontroller, either for dedicated use by the stimulus control module 710 or shared with the controller. The microprocessor or microcontroller can include components as would be understood by a worker skilled in the art, including CPU, memory, inputs, outputs, interrupt control, clock, and the like.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

As used herein, the term "about" refers to a +/−10% variation from the nominal value. It is to be understood that such a variation is always included in any given value provided herein, whether or not it is specifically referred to.

The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited. In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

The person of skill in the art will understand that the foregoing embodiments of the invention are examples and can be varied in many ways. Such present or future variations are not to be regarded as a departure from the spirit and scope of the invention, and all such modifications as would be apparent to one skilled in the art are intended to be included within the scope of the following claims.

I claim:

1. A system for emitting light, the light providing a desired light-induced physiological stimulus and a desired luminous stimulus, the system comprising:
   a plurality of first light-emitting elements configured to emit light of a first wavelength range, said plurality of first light-emitting elements responsive to a plurality of first control signals;
   said plurality of first light emitting elements including first set of blue LEDs and a second set of blue LEDs, said first set of blue LEDs having a first peak wavelength, said second set of blue LEDs having a second peak wavelength, said first peak wavelength at about 440 nm and said second peak wavelength at about 480 nm;
   one or more second light-emitting elements configured to emit light of a second wavelength range, the one or more second light-emitting element responsive to one or more second control signals; and
   a control system operatively coupled to said plurality of first light-emitting elements and the one or more second light-emitting elements,
   said control system configured to generate said plurality of first control signals and the one or more second control signals based on the desired light-induced physiological stimulus, the desired luminous stimulus, the first wavelength range and the second wavelength range to maintain a substantially constant luminous stimulus by modifying said plurality of first control signals to increase the intensity of said first set of blue LEDs while correspondingly modifying said second control signals to reduce the intensity of said second set of blue LEDs and said one or more second light emitting elements;
   wherein said control system further is configured to maintain said system emitted tight at said desired luminous stimulus while independently modifying said first set of blue LEDs, said second set of blue LEDs and said one or more second light-emitting elements.

2. The system of claim 1 wherein the physiological stimulus has one or more physiological effects selected from the group consisting of hormone metabolization, sleep control, circadian effects, organ activity, cell metabolization and immune system response.

3. The system of claim 1, wherein the luminous stimulus is selected from die group consisting of: colour, brightness, luminance, luminous flux, intensity, colour, correlated colour temperature and chromaticity.

4. The system of claim 1, wherein variation of the physiological stimulus includes varying emission of light having frequencies between about 420 nm and about 500 nm.

5. The system of claim 1, further comprising one or more sensors configured to provide one or more feedback signals to the controller, wherein the one or more sensors are selected from the group consisting of: temperature sensors, voltage sensors and optical sensors.

6. A method for controlling light to provide a desired light-induced physiological stimulus and a desired luminous stimulus, the method comprising the steps of:
   generating light having a first wavelength range at a first intensity, said first wavelength range being between about 440 nm and 570 nm, said light emitted by a first set of blue LEDs and a second set of blue LEDs, said first set of blue LEDs emitting said light at about 440 nm and said second set of blue LEDs emitting light at a wavelength above said first wavelength range;
   generating light having a second wavelength range at a second intensity;
   adjusting the first intensity through modification of the light of the first set of blue LEDs and the light of the second set of blue LEDs and adjusting the second intensity to generate mixed light having the desired light-induced physiological stimulus and the desired luminous stimulus;
   wherein said first set of blue LEDs and said second set of blue LEDs are independently controlled,
   substantially maintaining said desired luminous stimulus front the modified output of the first set of blue LEDs, second set of blue LEDs and the second intensity while independently adjusting both said first set of blue LEDs and said second set of blue LEDs.

7. The method of claim 6, wherein the physiological stimulus is varied with respect to one or more of time, duration and strength to achieve a desired effect.

8. The method of claim 6, wherein the physiological stimulus and the luminous stimulus are provided substantially simultaneously.

9. The method of claim 6, wherein the physiological stimulus and the luminous stimulus are provided substantially alternately in time by providing a substantially imperceptible variation of the light.

10. The method of claim 6, wherein the physiological stimulus has one or more physiological effects selected from the group consisting of: hormone metabolization, sleep control, circadian effects, organ activity, cell metabolization and immune system response.

11. The method of claim 6, wherein the luminous stimulus is selected from the group consisting of: colour, brightness, luminance, luminous flux, intensity, colour, correlated colour temperature, colour rendering index, and chromaticity.

* * * * *